US008647863B2

(12) United States Patent
Mayrhofer et al.

(10) Patent No.: US 8,647,863 B2
(45) Date of Patent: Feb. 11, 2014

(54) MINICIRCLE VECTOR PRODUCTION

(75) Inventors: Peter Mayrhofer, Vienna (AT);
Wolfgang Jechlinger, Vienna (AT);
Werner Lubitz, Kritzendorf (AT)

(73) Assignees: Gerhard Jechlinger, Osterreich (AT);
Peter Mayrhofer, Vienna (AT)

( * ) Notice: Subject to any disclaimer, the term of this patent is extended or adjusted under 35 U.S.C. 154(b) by 1539 days.

(21) Appl. No.: 10/556,069

(22) PCT Filed: May 4, 2004

(86) PCT No.: PCT/EP2004/004721
§ 371 (c)(1),
(2), (4) Date: Aug. 24, 2006

(87) PCT Pub. No.: WO2004/099420
PCT Pub. Date: Nov. 18, 2004

(65) Prior Publication Data
US 2007/0031378 A1 Feb. 8, 2007

(30) Foreign Application Priority Data
May 8, 2003 (AT) .................................. A 700/2003

(51) Int. Cl.
C12N 15/00 (2006.01)
A61K 48/00 (2006.01)
(52) U.S. Cl.
USPC ...................................... 435/320.1; 514/44 R
(58) Field of Classification Search
None
See application file for complete search history.

(56) References Cited

U.S. PATENT DOCUMENTS 6,143,530 A 11/2000 Crouzel et al.

FOREIGN PATENT DOCUMENTS

| WO | 96/00282 A1 | 1/1996 |
| WO | 9626270 A1 | 8/1996 |
| WO | 02/20823 A2 | 3/2002 |
| WO | 02/083889 A2 | 10/2002 |

OTHER PUBLICATIONS

See Jechlinger et al, J Mol Microbiol Biotechnol. 8(4):222-31, 2004.*
Mayrhofer et al, J Gene Med. 10(11):1253-69, 2008.*
Examination Report dated May 7, 2009, for EP Application No. 04730974.5-2401.
Jan A. Gossen et al, "Plasmid Rescue from Transgenic Mouse DNA Using LacI Repressor Protein Conjugated to Magnetic Beads", BioTechniques, 1993, 14(4): 624-629.
Noaman Hasan et al., "Construction of lacIts and LacI$^q$ts expression plasmids and evaluation of the thermosensitive lac repressor", Gene, 1995, 163: 35-40.
Joakim Lundeberg et al., "Affinity Purification of Specific DNA Fragnments Using a lac Repressor Fusion Protein", Genet. Anal. Techn. Appl., 1990, 7:47-52.
Steven W. Granger et al., "Purification of Moloney Murine Leukemia Virus Chromatin from Infected Cells by an Affinity Method", J. Biomed. Sci., 2001, 8: 278-289.
John R. Sadler et al., "Plasmids Containing Many Tandem Copies of a Synthetic Lactose Operator", Gene, 1980, 8: 279-300.
A-M Darquet et al., "Minicircle: an improved DNA molecule for in vitro and in vivo gene transfer", Gene Therapy, 1998, 6: 209-218.
Third Party Observations filed in corresponding EP Patent Application No. 10157309.5 on May 31, 2011 (in the name of Austria Wirtschaftsservice GmbH).
Peter J. Schatz, "Use of Peptide Libraries to Map the Substrate Specificity of a Peptide-Modifying Enzyme: A 13 Residue Consensus Peptide Specifies Biotinylation of Escherichia coli", Bio/Technology, 1993, 11: 1138-1143.
John R. Sadler et al., "A Perfectly Symmetric lac Operator Binds the lac Repressor Very Tightly", Proceedings of the National Academy of Science of the USA, 1983, 80: 6785-6789.
Leo Eberl et al., "Analysis of the multimer resolution system encoded by the parCBA operon of broad-host-range plasmid RP4" Molecular Microbiology, 1994, 12(1): 131-141.
EMBOSS Needle-Alignment, retrieved from http://www.ebi.ac.uk on Mar. 27, 2012.
NCBI Reference Sequence NC_001416.1, Enterobacteria phage lambda, complete genome, retrieved from http://www.ncbi.nlm.nih.gov/nuccore/9626243?report=fasta on Mar. 27, 2012.
Michiyo Mizuuchi et al., "Integrative recombination of bacteriophage λ: Extent of the DNA sequence involved in attachment site function", Proc. Natl. Acad. Sci. USA, 1980, 77(6): 3220-3224.
Luz-Maria Guzman et al., "Tight Regulation, Modulation, and High-Level Expression by Vectors Containing the Arabinose $P_{BAD}$ Promoter", Journal of Bacteriology, 1995, 177(14): 4121-4130.
Kristala L. Jones et al., "Low-Copy Plasmids can Perform as Well as or Better Than High-Copy Plasmids for Metabolic Engineering of Bacteria", Metabolic Engineering, 2000, 2: 328-338.
Thomas A. Kunkel et al., "Rapid and Efficient Site-Specific Mutagenesis without Phenotypic Selection", Methods in Enzymology, 1987, 154: 367-382.
Thomas A. Kunkel et al., "Efficient Site-Directed Mutagenesis Using Uracil-Containing DNA", Methods in Enzymology, 1991, 204: 125-139.
M. Molas et al., "Single-stranded DNA condensed with poly-L-lysine results in nanometric particles that are significantly smaller, more stable in physiological ionic strength fluids and afford higher efficiency of gene delivery than their double-stranded counterparts", Biochimica et Biophysica Acta, 2002, 1572: 37-44.
Robert J. Zagursky et al., "Cloning vectors that yield high levels of single-stranded DNA for rapid DNA sequencing", Gene, 1984, 27: 183-191.

(Continued)

Primary Examiner — Michael Burkhart
(74) Attorney, Agent, or Firm — Sughrue Mion, PLLC

(57) ABSTRACT

A plasmid is provided comprising the following functional units: a prokaryotic origin of replication, a marker sequence, two specific recombinase recognition sequences and a multiple cloning site, whereby it comprises a gene coding for a sequence specific recombinase, whereby the units are arranged on the plasmid in such a way that the plasmid is divided into a miniplasmid and a minicircle upon expression of the sequence specific recombinase, said miniplasmid comprising the prokaryotic origin of replication, the marker sequence and the gene for the sequence specific recombinase and said minicircle comprising the multiple cloning site.

22 Claims, 10 Drawing Sheets

(56) References Cited

OTHER PUBLICATIONS

Brian W. Bigger et al., "An *ara*C-controlled Bacterial *cre* Expression System to Produce DNA Minicircle Vectors for Nuclear and Mitochondrial Gene Therapy", The Journal of Biological Chemistry, 2001, 276(25): 23018-23027.

Zhi-Ying Chen et al., "Minicircle DNA Vectors Devoid of Bacterial DNA Result in Persistent and High-Level Transgene Expression in Vivo", Molecular Therapy, 2003, 8(3): 495-500.

P. Kreiss et al., "Production of a new DNA vehicle for gene transfer using site-specific recombination", Appl. Molecular Biotechnol., 1998, 49: 560-567.

W. Lubitz et al., "Extended recombinant bacterial ghost system", Journal of Biotechnology, 1999, 73: 261-273.

Michael P. Szostak et al., "Bacterial ghosts: non-living candidate vaccines", Journal of Biotechnology, 1996, 44: 161-170.

* cited by examiner

A:

B

A:

B:

SEQUENCE LISTING

```
<160> NUMBER OF SEQ ID NOS: 14

<210> SEQ ID NO 1
<211> LENGTH: 32
<212> TYPE: DNA
<213> ORGANISM: Artificial Sequence
<220> FEATURE:
<223> OTHER INFORMATION: Primer SIPI5

<400> SEQUENCE: 1
cagcagaagc ttgttttggc ggatgagaga ag                              32

<210> SEQ ID NO 2
<211> LENGTH: 39
<212> TYPE: DNA
<213> ORGANISM: Artificial Sequence
<220> FEATURE:
<223> OTHER INFORMATION: Primer pSIPI3

<400> SEQUENCE: 2
agatctctgc tggcggccgc ggttgctggc gcctatatc                       39

<210> SEQ ID NO 3
<211> LENGTH: 34
<212> TYPE: DNA
<213> ORGANISM: Artificial Sequence
```

-continued

```
<220> FEATURE:
<223> OTHER INFORMATION: Primer resolution site 1 (5res1)

<400> SEQUENCE: 3
cagcagctgc agccttggtc aaattgggta tacc                              34

<210> SEQ ID NO 4
<211> LENGTH: 31
<212> TYPE: DNA
<213> ORGANISM: Artificial Sequence
<220> FEATURE:
<223> OTHER INFORMATION: Primer resolution site 1 (3res1)

<400> SEQUENCE: 4
ctgctgaagc ttgcacatat gtgggcgtga g                                 31

<210> SEQ ID NO 5
<211> LENGTH: 36
<212> TYPE: DNA
<213> ORGANISM: Artificial Sequence
<220> FEATURE:
<223> OTHER INFORMATION: Primer resolution site 2 (5res2)

<400> SEQUENCE: 5
cagcaggcgg ccgcccttgg tcaaattggg tatacc                            36

<210> SEQ ID NO 6
<211> LENGTH: 31
<212> TYPE: DNA
<213> ORGANISM: Artificial Sequence
<220> FEATURE:
<223> OTHER INFORMATION: Primer resolution site 2 (3res2)

<400> SEQUENCE: 6
ctgctgagat ctgcacatat gtgggcgtga g                                 31

<210> SEQ ID NO 7
<211> LENGTH: 29
<212> TYPE: DNA
<213> ORGANISM: Artificial Sequence
<220> FEATURE:
<223> OTHER INFORMATION: Primer 5ori

<400> SEQUENCE: 7
cagcaggccg gctgagcaaa aggccagca                                    29

<210> SEQ ID NO 8
<211> LENGTH: 41
<212> TYPE: DNA
<213> ORGANISM: Artificial Sequence
<220> FEATURE:
<223> OTHER INFORMATION: Primer 3ori

<400> SEQUENCE: 8
tgctgcgcgg ccgctagaaa agatcaaagg atcttcttga g                      41

<210> SEQ ID NO 9
<211> LENGTH: 30
<212> TYPE: DNA
<213> ORGANISM: Artificial Sequence
<220> FEATURE:
<223> OTHER INFORMATION: Primer BADKLysfw

<400> SEQUENCE: 9
attccgacta gtcaagccgt caattgtctg                                   30
```

```
<210> SEQ ID NO 10
<211> LENGTH: 30
<212> TYPE: DNA
<213> ORGANISM: Artificial Sequence
<220> FEATURE:
<223> OTHER INFORMATION: Primer BADKlysrev

<400> SEQUENCE: 10
agccctagat ctttattttt gctgctgcgc                                      30

<210> SEQ ID NO 11
<211> LENGTH: 30
<212> TYPE: DNA
<213> ORGANISM: Artificial Sequence
<220> FEATURE:
<223> OTHER INFORMATION: Primer BADparAfw

<400> SEQUENCE: 11
atagaaccat ggcgacgcga gagcaacaac                                      30

<210> SEQ ID NO 12
<211> LENGTH: 30
<212> TYPE: DNA
<213> ORGANISM: Artificial Sequence
<220> FEATURE:
<223> OTHER INFORMATION: Primer BADparArev

<400> SEQUENCE: 12
agccctctgc agttattttt gctgctgcgc                                      30

<210> SEQ ID NO 13
<211> LENGTH: 37
<212> TYPE: DNA
<213> ORGANISM: Artificial Sequence
<220> FEATURE:
<223> OTHER INFORMATION: Primer HCNparAfw

<400> SEQUENCE: 13
accgaactgc agctacacca tacccgtttt tttgggc                              37

<210> SEQ ID NO 14
<211> LENGTH: 36
<212> TYPE: DNA
<213> ORGANISM: Artificial Sequence
<220> FEATURE:
<223> OTHER INFORMATION: Primer HCNparArev

<400> SEQUENCE: 14
agccctctgc agaagctttt atttttgctg ctgcgc                               36
```

MINICIRCLE VECTOR PRODUCTION

This is a U.S. national stage entry of Application No. PCT/EP2004/004721 filed May 4, 2004.

The present invention relates to a plasmid comprising the following functional units:
a prokaryotic origin of replication,
a marker sequence,
two specific recombinase recognition sequences and
a multiple cloning site, as well as a kit for the production of a therapeutically useful protein, a minicircle, a pharmaceutical composition and a method for the production of a therapeutically useful protein.

The application of efficient delivery systems for DNA vaccines or somatic gene transfer is desirable in modern vaccine design. Therefore many application modes and formulations are under investigation to ensure optimal delivery of plasmid DNA for gene transfer. Examples are cationic liposomes, cationic poly-L-lysins, polyethylenamine, polymeric vesicles, naked DNA alone and microbial carriers such as replication deficient viruses.

However, plasmid DNA used for gene transfer and DNA vaccination has the disadvantage of carrying an antibiotic resistance marker and a bacterial origin of replication which may be shed into the environment due to the clinical use. Due to this dissemination of recombinant bacterial DNA endogenous *Enterobacteriacae* may acquire the DNA leading to replication and further uncontrolled spread of antibiotic resistance genes between different species and genera (horizontal gene transfer). Therefore efforts have been made to overcome this biosafety problem.

Minicircle DNA for nonviral gene transfer has been described which contain only the therapeutic expression cassette. Furthermore it has been shown that those minicircles besides their advantages for biosafety show improved gene transfer and bioavailability properties due to the small size (Darquet, A. M. et al. 1997. A new DNA vehicle for nonviral gene delivery: supercoiled minicircle. Gene Ther. 4:1341-9; Darquet, A. M. et al. 1999. Minicircle: an improved DNA molecule for in vitro and in vivo gene transfer. Gene Ther. 6:209-18). Such minicircles may be derived from in vivo approaches where a recombinase like the bacteriophage λ Int integrase, the Cre recombinase of bacteriophage P1 or the ParA resolvase recognises corresponding short sequences and excises DNA sequences encoded between them. If the origin of replication and the antibiotic resistance gene is placed between the recombinase recognition sequences, the recombinase divides the original plasmid into two parts: a replicative miniplasmid and a minicircle carrying only the sequences of interest. In vitro procedures are also available for the production of minicircle DNA like restriction digestion followed by ligation. However, those procedures would be extremely expensive and very difficult to scale up for industrial use. In contrast to the in vitro approach in vivo recombination is simple, inexpensive and only requires a recombinase to be induced in sufficient amounts.

In Bigger et al. (2001. An araC-controlled Bacterial cre Expression System to Produce DNA Minicircle Vectors for Nuclear and Mitochondrial Gene Therapy, J. Biol. Chem. 276:23018-27) minicircles are produced comprising only gene expression elements whereby an original plasmid comprising an origin of replication, a eucaryotic expression cassette, a marker sequence and two loxP sites as recombinase recognition sequences is transfected into a bacteria which is recombinant for the Cre recombinase, a bacteriophage P1 derived integrase catalysing site specific recombination between direct repeats of 34 base pairs (loxP sites). After expression of the Cre recombinase the original plasmid is divided into a mini plasmid and a minicircle said minicircle comprising only the eucaryotic expression cassette. The resulting plasmid products are subjected to specific restriction enzymes which cut the miniplasmid but not the minicircle. Undigested supercoiled minicircle can then be density-separated from the linear original plasmid and excised miniplasmid on a cesium chloride gradient using the intercalating agent ethidium bromide. In order to test the expression cassette of the minicircle within mammalian cells the minicircle was transfected together with LipofectAMINE into the cells. It is mentioned that said Cre-mediated recombination system employed resulted in a minimal construct size comparable to phage λ integrase-mediated recombination which leads to minicircles with higher transfection efficiency.

In Darquet et al. (1997. A new DNA vehicle for nonviral gene delivery: supercoiled minicircle. Gene Ther. 4:1341-9) the production of minicircles comprising only the expression cassette is described. Here the original plasmid is transfected into a bacterium which is recombinant for the phage λ integrase which mediates the recombination of the plasmid into miniplasmid in minicircle. The plasmid products were digested with restriction enzymes which produce linear miniplasmid and original plasmid and leave the minicircle supercoiled which was purified on density gradients. However, it is mentioned that the yield of unrecombined plasmid was around 40% of the starting material. It is suggested to improve the yield of recombination which would have to be close to 100% for example by optimising the culture conditions of the recombinant bacteria and by overexpressing the integrase.

Kreiss et al. (1998. Production of a new DNA vehicle for gene transfer using site-specific recombination. Appl. Microbiol. Biotechnol. 49:560-7) relates to the production of minicircles which are produced by recombination of an original plasmid driven by a bacteriophage λ integrase present in the bacteria into which the original plasmid is transfected. However, minicircle multimers were also produced and comprised up to 30% of all minicircles synthesised. In order to increase the minicircle production efficiency parABCDE' locus from plasmid RK2 was introduced into the minicircle fragment and a parA gene encoding a resolvase that catalyses the recombination at a multimer resolution site in the parAB-CDE' locus was also introduced into the bacteria. The parA resolvase together with the parABCDE' locus lead to the production of minicircle dimers of less than 2% of all minicircles. However, it is also here mentioned that the efficiency of minicircle production must be further increased and it is suggested to improve the purification of the minicircle from unresolved plasmid and miniplasmid.

Darquet et al. (1999. Minicircle: an improved DNA molecule for in vitro and in vivo gene transfer. Gene Ther. 6:209-18) relates to the production of minicircle whereby a method is described which should improve the minicircle production efficiency: The original plasmid is transfected into a bacteria which comprises a gene for the phage λ integrase which catalyses the recombination at the attP/attB sites present on the original plasmid in order to produce minicircle and miniplasmid. The minicircles comprise a gene expression cassette using a strong human cytomegalovirus immediate-early enhancer/promoter. The plasmid productions were digested with restriction enzymes which cut only the miniplasmid and the unrecombined plasmid but not the corresponding minicircle. Supercoiled minicircles were then isolated by CsCl-ethidium bromide density gradient centrifugation. It was found that the minicircles comprising the specific promoters produced better results with strong gene expression compared to unrecombined plasmid or larger plasmids.

However, the drawback of the methods according to the above mentioned documents is the low efficiency of minicircle production compared to original plasmids. This problem has been discussed in the above documents, however, a near to 100% production of minicircle was not achieved. Therefore, there is the need for a plasmid from which near to 100% minicircle is able to be produced as well as a method for such a highly efficient minicircle production.

The WO 02/083889 A2 relates to a plasmid which produces after reaction with a recombinase a minicircle and a miniplasmid, whereby the minicircle comprises a DNA sequence of interest, not, however, any further regulatory sequences. These regulatory sequences are comprised on the miniplasmid. Therefore, a recombinase is added to the reaction and is not comprised on the plasmid.

The WO 96/00282 A1 relates to the expression of genes in *Streptomyces* strains whereby an expression cassette is disclosed which comprises among other elements a minicircle, whereby this minicircle is, however, defined as an integration element which is produced from the *Streptomyces coelicolor* and which is used to lead the insertion of the vector into the *Streptomyces* genome.

The aim of the present invention is therefore the construction of a plasmid which is used in the method for the production of a minicircle whereby a high efficiency in minicircle production is obtained.

This object is solved according to the present invention by a plasmid comprising the following functional units:
a prokaryotic origin of replication,
a marker sequence,
two specific recombinase recognition sequences and
a multiple cloning site, whereby it further comprises a gene coding for a sequence specific recombinase, and
whereby the units are arranged on the plasmid in such a way that the plasmid is divided into a miniplasmid and a minicircle upon expression of the sequence specific recombinase, said miniplasmid comprising the prokaryotic origin of replication, the marker sequence and the gene for the sequence specific recombinase and said minicircle comprising the multiple cloning site. With this plasmid a high efficiency in the production of minicircle is achieved due to the fact that the gene coding for a sequence specific recombinase is present on the (original) plasmid. This results in a high plasmid recombination and minicircle production which can reach under optimal conditions up to 100%. This is partly due to the control of the expression of recombinase which ensures that the recombination is not carried out too early so that a limitation of production of minicircle does not occur. A further reason for an increase of efficiency of minicircle production compared to the prior art is the fact that the known plasmid containing the recombinase present in the bacteria and the second separate plasmid from which the miniplasmid and minicircle are derived are often present in the bacteria in different amounts. Therefore, in the known methods according to the state of the art the production of minicircle is often limited by the number of recombinase plasmid. The inventive plasmid comprising the units of a miniplasmid and the units of the minicircle as well as the gene coding for the recombinase has not been described or made obvious in the state of the art. Furthermore, according to the state of the art, an increase of efficiency was aimed at by optimising the bacterial culture conditions and by developing alternative methods for high copy promoters used in the eucaryotic expression cassette present on the minicircle and methods for the purification of the minicircle. However, to provide a plasmid comprising not only the various functional units of miniplasmid and minicircle but also the gene coding for a sequence specific recombinase has not been mentioned or made obvious in the state of the art.

Of course the inventive plasmid may comprise further regulatory or functional units, however, the units defined above are the minimum for an efficient production of minicircle.

The prokaryotic origin of replication and a marker sequence are necessary for the production of the plasmid in for example bacteria. Various prokaryotic origins of replication are known to the person skilled in the art who will be able to select according to the bacteria culture, the culture conditions and the type of plasmid the optimal prokaryotic origin of replication. The marker sequence may be any of the well-known sequences which are used for being able to detect bacteria comprising the plasmid or to control the growth of bacteria comprising the plasmid compared to bacteria which have not been transfected with the plasmid in question. For example antibiotic resistance genes, heavy metal resistancies, auxotrophic selection markers, genes which produce a substance necessary for bacterial growth, etc. may be used.

The term "gene coding for a sequence specific recombinase" relates to any sequences necessary for the expression of the recombinase e.g. a promoter, termination sequence etc. The recombinase itself may be any recombinase which is able to catalyse the recombination of the original plasmid into miniplasmid and separate minicircle at defined recognition sequences.

The term "two specific recombinase recognition sequences" relates to sequences which are recognised by the recombinase. The fact that two recognition sequences are present means that the recognition sequences must be arranged on a plasmid in such way that the recombinase catalyses the production of a miniplasmid and a minicircle. Of course, it is possible that the recognition sequences are derived from one recognition sequence into which for example a cloning site is inserted which means that in fact the sequences which are recognised by the recombinase should flank the multiple cloning site which will then provide the minicircle. Of course, it is possible that the produced minicircle comprises at least part of the one and/or the other recognition sequence.

The term "multiple cloning site" refers to a site comprising at least 2 sites for restriction enzymes, however, preferably it comprises a number of sites for various restriction enzymes.

As known from the state of the art the produced minicircle comprises only the multiple cloning site without any of the prokaryotic regulation units e.g. the prokaryotic origin of replication, the marker sequence and without the gene coding for the specific recombinase. With this the production of a small minicircle is achieved whereby the smaller the minicircle the more efficient is the uptake for example in the mammalian cells.

Preferably, a gene coding for a specific protein, preferably a therapeutically useful protein, is inserted into the multiple cloning site. Since the minicircle will be mainly used for therapeutic reasons the multiple cloning site will preferably comprise a gene coding for a therapeutically useful protein. However, it is of course possible to insert any gene coding for any protein in which case the minicircle can be used for detection methods, biochemical pathway studies etc.

Still preferred the plasmid further comprises a minicircle, and/or miniplasmid identification sequence for the identification and isolation of the minicircle. The identification sequence provides an efficient way of separating the minicircle from the miniplasmid which further enhances the efficiency of minicircle production. The minicircle or miniplasmid identification sequence is any sequence which will be present on the minicircle and not on the miniplasmid (or vice versa) and which will allow the identification and isolation of the minicircle (or the removal of the miniplasmid). The description below will concentrate on minicircle identification sequences but will be also applicable to miniplasmid identification sequences or to the presence of both, minicircle and miniplasmid identification sequences. This may be a specific sequence which will bind to a given ligand so that a minicircle will be complexed with the ligand after which the complex will be separated from the miniplasmid, cellular components, etc. for example by immobilisation of the ligand.

If the mixture from minicircle and miniplasmid produced in vivo should be separated by interaction chromatography, one of the two DNA molecules should have the specific recognition sequence. To achieve a separation, the recognition sequence may principally be integrated in the minicircle or miniplasmid. If the recognition sequence is integrated in the miniplasmid, only the target sequence and the Res-site (the product of the recombination between res1 and res2 site) may be found on the minicircle. In this process the minicircle DNA is situated in the eluate of the affinity chromatography, while the miniplasmid DNA is bound to the matrix (the miniplasmid DNA may for instance then be eluted from the column by increasing the temperature from <30° C. to ≥42° C.; thereby the column is regenerated and a new purification process starts). For the purification of the minicircle DNA the eluate should be applied to a following column. This column may for instance be a column with an ion exchange matrix or a matrix for hydrophobic interaction chromatography, or for size exclusion chromatography, respectively, etc. In principle, any chromatography process may be employed, which is used for isolating DNA molecules.

In combination with the immobilisation of the minicircle DNA and the subsequent protein E mediating lysis this purification process provides the advantage that possibly occurring capacity problems of the affinity chromatography matrix may be solved. As the most part of the cytoplastmatic molecules (including miniplasmid DNA) are expelled into the culturing medium during lysis, only a compartively small number of DNA miniplasmids (about 10%) has to be bound to the matrix.

According to a further advantageous embodiment the identification sequence is a sequence which is able to specifically bind to a protein in order to form a stable DNA-protein complex. The term "specifically bind" defines that this identification sequence may not be any sequence which binds by chance and unspecifically to any protein with which it is brought into contact. The identification sequence ensures a specific binding to a chosen protein in order to form a stable DNA protein complex. This identification sequence is able to specifically bind to a protein ensures the preparation of the minicircle from the miniplasmid by bringing a minicircle into contact with the specific protein to which the identification sequence will bind. For the protein DNA interaction chromatography specific DNA binding proteins are immobilised on a matrix for affinity chromatography (e.g. the repressor of Lactose Operon, the repressor of the bacteriophage lambda, or of bacteriophage 434, etc.). The corresponding recognition sequence as appropriate (e.g. the operator sequence of the promoter of the Lactose Operon, of the $P_L$ or $P_R$ promoters of the bacteriophage lambda or corresponding sequences of bacteriophage 434) is located on the DNA molecule that specifically should bind to this matrix. To again separate specifically bound DNA molecules from the affinity chromatography matrix by temperature shifting (elution buffer with corresponding temperature), thermally instable mutants of the mentioned repressor molecules may be used. The recognition sequences may be separated from each other by a spacer. The spacer sequence may be chosen arbitrarily (unrelated sequence) and serves for optimising the interaction between the temperature-sensitive repressor and the corresponding operator. The separation may occur by immobilisation of the formed complex, by separation according to particle size, e.g. filtration or other methods well-known to the person skilled in the art whereby the separation method will depend on the protein selected.

Still preferred said identification sequence is a lac operator site which specifically binds to a LacI repressor protein. The lac operator site is a sequence which binds to a LacI repressor protein in order to form a stable DNA protein complex which then can be separated from the miniplasmid. Therefore, an efficient system is provided for the production and also separation of minicircles.

According to the preferred embodiment the sequence specific recombinase is selected from the group consisting of bacteriophage lambda Int integrase, Cre recombinase of bacteriophage P1 and the ParA resolvase. These recombinases have shown to provide good results in the production of minicircles whereby each recombinase shows specific characteristics. For example the lambda integrase system needs the integration host factor for recombination, the ParA resolvase needs topoisomerases which are present in all bacteria. In order to resolve the recombination complexes the Cre mediated recombination system on the other hand has the advantage that it results in a very small recognition site for example of only 34 base pairs thus producing a minimal construct site. The person skilled in the art will select the optimal recombinase according to these differences and their specific characteristics.

Advantageously, the specific recombinase recognition sequences are selected from the group consisting of lambda attachment sites (att sites) and resolution sites (res sites) from Multimer Resolution Systems. These recognition sequences will depend on the recombinase selected so that according to the characteristics needed for the recombination system the person skilled in the art will select the optimal recognition sequences and recombinase.

A preferred plasmid further comprises a regulatory element for the expression of the recombinase. By providing a regulatory element for the expression of the recombinase the expression of the recombinase can be either inhibited or induced. This allows the expression of the recombinase to occur when necessary. With this system the plasmid can be produced in great quantities before the expression of the recombinase is induced so that a maximum efficiency of minicircle production is achieved. Various regulatory elements are well-known to the person skilled in the art and the selection thereof will depend on the host in which the plasmid is produced in other vectors.

Preferably, the regulatory element for the recombinase comprises a strong promoter. This allows sufficient expression of recombinase in order to catalyse the recombination of the total amount of plasmid present in the sample in order to achieve a maximum yield of minicircle.

Still preferred the regulatory element is a transcriptional control system of an araB promoter of an araBAD operon. This control system will inhibit expression of the recombinase as long as no arabinose is present in the culture medium. Upon addition of arabinose for example L-arabinose to the culture medium the recombinase expression is induced. This is a very simple and efficient method of regulating the expression of recombinase.

Preferably, the marker gene is an antibiotic resistant gene. This is a well-known method in order to select the bacteria transfected with the plasmid comprising a marker gene in order to efficiently produce the plasmid in high copy numbers.

Advantageously, the prokaryotic origin of replication is a high copy number origin of replication, preferably from plasmid pUC19. As for the strong promoter mentioned above this will provide an optimal plasmid which will be produced in abundance in a bacteria. The yield of minicircle production is optimised by producing a high copy number of plasmid in the bacteria cell.

Preferably, the plasmid according to the present invention comprises an origin of replication in the minicircle. The recognition sequence for the protein DNA interaction chromatography may consist of repeats of operator sequences (e.g. lacOs), which are separated by a spacer. This spacer may consist of any sequence. Preferably, this spacer is an origin of replication (ori) for bacteriophages specific for $E.\ coli$ (for example filamentous bacteriophages, as e.g. f1, M13, fd, icosaedric bacteriophages, as e.g. φX174). Such an origin of replication serves for the production of single stranded DNA, which may be used for the systematic introduction of mutations into the target sequence (therpeutical sequence or sequence for vaccination) (Kunkel et al., Meth. Enzymol. 204 (1991), 125-139; Meth. Enzymol. 154 (1987), 367-382). A further application of a bacteriophage origin of replication is the production of a single stranded DNA (ssDNA) for gene transfer. With the assistance of a ssDNA origin of replication (e.g. the above mentioned filamentous bacteriophage or the φX174 origin) ssDNA of the minicircle sequence may be produced, provided that the origin of replication is located on the minicircle DNA. Depending on the origin of replication used corresponding auxiliary factors may be necessary for producing ssDNA (e.g. protein A in combination with φX174 ori). For the isolation of the single stranded DNA by affinity chromatography ssDNA binding proteins (e.g. protein J of bacteriophage φX174) might be used, or ssDNA primer complementary to a sequence of the ss-minicircle DNA, e.g. Res1-site. The application of ssDNA may lead to a further improvement of the gene transfer capacity of minicircle DNA (Molas et al., Biochim. Biophys. Acta 1572 (2002) 37-44).

If a bacteriophage origin of replication is integrated into the starting plasmid, it will be located on the minicircle DNA after recombination. Therefore, the minicircle DNA does not have a bacterial replication origin, but an origin of replication originating from a non-lysogenic bacteriophage. This bacteriophage is harmless in regard to biological safety, as this may not lead, without corresponding auxiliary factors (protein factors or helper phages) to a proliferation of the minicircle DNA in prokaryotic or eukaryotic cells.

A further aspect relates to a kit for the production of a therapeutically useful DNA molecule which comprises
the plasmid according to the present invention and
a protein which is able to bind to the identification sequence of the plasmid in order to form a stable DNA-protein complex, whereby the protein is optionally immobilised to a solid support. Similar to the kit above this kit comprises a system for separating the minicircle from the miniplasmid whereby a protein is provided to which the identification sequence of the minicircle specifically binds in order to form a stable DNA protein complex which can then be separated from the miniplasmid.

In both cases the single strand and the protein, respectively, can be immobilised to a solid support which may for example be a column, a membrane, a slide, a filter etc. In this case the sample is brought into contact with the solid support after the expression of the recombinase after which the solid support is preferably washed so that only minicircle remains on the solid support. In order to produce isolated minicircles a further elution step can be carried out.

Preferably, the protein is a LacI repressor protein, preferably a mutant LacI repressor protein. This protein binds to the lac operon which can be provided on the minicircle as identification sequence. This system, therefore, provides for a highly efficient way of separating minicircle and miniplasmid. The LacI repressor protein can be a mutant whereby the protein is preferably mutated in such way that the binding of the repressor protein to the lac operon can be regulated. One possibility is to provide a mutant repressor protein which is stable only at a certain temperature. Above or below this temperature the repressor-lac operon complex is not stable so that the minicircle is detached from the protein. This is a very elegant way for providing a regulation of immobilisation—elution of minicircles.

Advantageously, the protein is fused to a tag for the immobilisation to a solid support. This allows the use of any selected protein since the immobilisation will be determined by the tag so that any chosen DNA-protein complex may be designed.

Still preferred the protein is fused to a hydrophobic, membrane anchoring peptide. In this case the protein is immobilised on the membrane of the bacteria which allows the immobilisation of the minicircle on the membrane. The bacteria membrane can then be broken open in order to have the cytoplasmatic material comprising the miniplasmid an the original plasmid expelled from the bacteria. The remaining bacterial ghosts retain all of the structural features of the cell and the minicircles. This bacterial ghost is an excellent adjuvant enhancing T-cell activation and mucosal immunity.

Advantageously, the plasmid comprises a gene coding for the protein which forms the DNA-protein complex, preferably a gene coding for the LacI repressor protein. By providing the gene coding for this protein on the same plasmid preferably under the control of the promoter which also controls the recombinase the efficient expression of the protein is ensured and it is not necessary to foresee an additional way of providing the protein for example in the bacteria.

Preferably, the plasmid comprises a sequence coding for a hydrophobic membrane anchoring peptide. This membrane anchoring peptide may be the protein of the DNA-protein complex or a part of the protein or it may also be a separate protein which will be fused to the protein of the DNA-protein complex. The hydrophobic membrane anchoring peptide allows the immobilisation of the DNA-protein complex in the bacterial inner membrane. Therefore, once the minicircles are produced they are attached to the inner membrane of the bacteria in which the recombinase was expressed and the plasmid was produced. The advantage thereof lies in the fact that not only the production of the minicircle occurs in vivo but also the separation of minicircle from the miniplasmid for example by breaking open the bacterial membrane so that the cytoplasmic material is expelled from the bacteria cell. A further advantage lies in the fact that the resulting bacterial ghost consisting of the cell wall and the minicircle attached to the inner membrane constitutes an efficient adjuvant so that the minicircle comprising for example a therapeutically useful protein can be administered in form of these bacterial ghosts without any further DNA extraction or packaging procedures.

For breaking open the bacteria cell the kit preferably further comprises a plasmid with an inducible lysis gene and a culture of recombinant bacteria transfected with said plasmid, respectively. The inducible lysis gene induces lysis of the bacteria in order to break open a cell wall as mentioned above. The plasmid with the inducible lysis gene may be the original plasmid comprising thus additionally the units for the miniplasmid and the minicircle, however, it is possible to provide also a separate plasmid either isolated or transfected into a culture of bacteria. Since the lysis gene is inducible the bacteria can be cultured together with the original plasmid until the sufficient number of plasmid is produced after which the expression of recombinase can be induced. Once, the recombinase has produced the minicircle and miniplasmid the lysis gene can be activated in order to separate the minicircle as mentioned above. This kit provides an all in vivo system for a highly efficient production of minicircles.

Advantageously, the lysis gene is the lysis gene E of bacteriophage PhiX174. This is shown to be an optimal way for the above in vivo minicircle production.

An advantageous kit comprises a culture of bacteria specific for the expression and function of the recombinase. Since a specific recombinase in general needs specific factors for the expression and function of the recombinase, it is more efficient to provide the bacteria already comprising these factors instead of adding these factors into any other selected bacteria.

Still preferred the kit further comprises arabinose. This will be optimal in the case that the plasmid comprises a regulatory element which is induced upon adding of arabinose whereby the arabinose is preferably L-arabinose.

A further aspect of the present invention relates to a minicircle which is derivable from the inventive plasmid as mentioned above comprising
a multiple cloning site and
a gene coding for a therapeutically useful protein inserted into the multiple cloning site,
whereby the minicircle is attached to a bacterial ghost over a hydrophobic membrane anchoring peptide. Also for this aspect the same definitions and preferred embodiments as mentioned above apply. By providing this inventive minicircle a highly efficient tool for DNA therapy is provided since the bacterial ghost is an efficient adjuvant.

In view of these advantages a further aspect of the present application relates to a pharmaceutical composition comprising the above defined inventive minicircle and a pharmaceutically acceptable carrier. Due to the bacterial ghost it is not necessary to add further adjuvants, however, depending on a concentration of minicircle and the DNA to be administered it is of course possible to add a further adjuvant as well as any other additional substances usually present in pharmaceutical compositions, as salts, buffers, stabilisers, colouring substances, flavours etc.

A further aspect of the present application relates to a method for the production of a therapeutically useful DNA molecule which comprises the following steps
transfecting the plasmid according to the present invention into bacteria which are able to replicate the plasmid,
culturing the bacteria during which the recombinase is expressed so that miniplasmids and minicircles are produced and
isolating the minicircles. Also for this aspect the above definitions and preferred embodiments apply. As already mentioned above this method allows a highly efficient production of minicircle resulting in a high yield, preferably up to 100%. This has not been able to be achieved with the methods according to the state of the art whereby the high yield is mainly due to the fact that the recombinase is present on the plasmid comprising the recombinase recognition sequences.

Preferably, the minicircles are isolated by using the minicircle identification sequence. This allows an optimisation of the method and increases the yield of minicircle production. Here, again the above definitions and preferred embodiments apply.

Advantageously, the minicircles are isolated by immobilisation to a solid support, preferably a chromatography column. Thereby, not only a high yield of minicircle production is achieved but also the method can be carried out without additional high-tech means and can be carried out in any laboratory. The sample with the recombinase reaction product is simply added to the solid support, e.g. the chromatography column, preferably washed after which the minicircle may be eluted as already described above.

Alternatively, the protein recognising the minicircle identification sequence may also be expressed in the bacteria and anchored in the bacterial membrane so as to be capable of binding to the minicircles.

Still preferred the recombinase is expressed upon induction of the regulatory element, preferably by adding arabinose to the culture medium. As already mentioned above this allows production of the original plasmid in a first step and only once a sufficient amount of original plasmid has been produced the expression of the recombinase is induced by activating the regulatory element for example by adding arabinose to the culture medium so that only at this moment the original plasmid is separated into miniplasmid and minicircle.

The invention is further described in more detail with the following examples and figures to which the invention is however not limited whereby FIG. 1 shows a precursor of the plasmids used in the present invention;

EXAMPLE 1

Plasmids, Bacterial Strains and Growth Conditions

Figure 1:
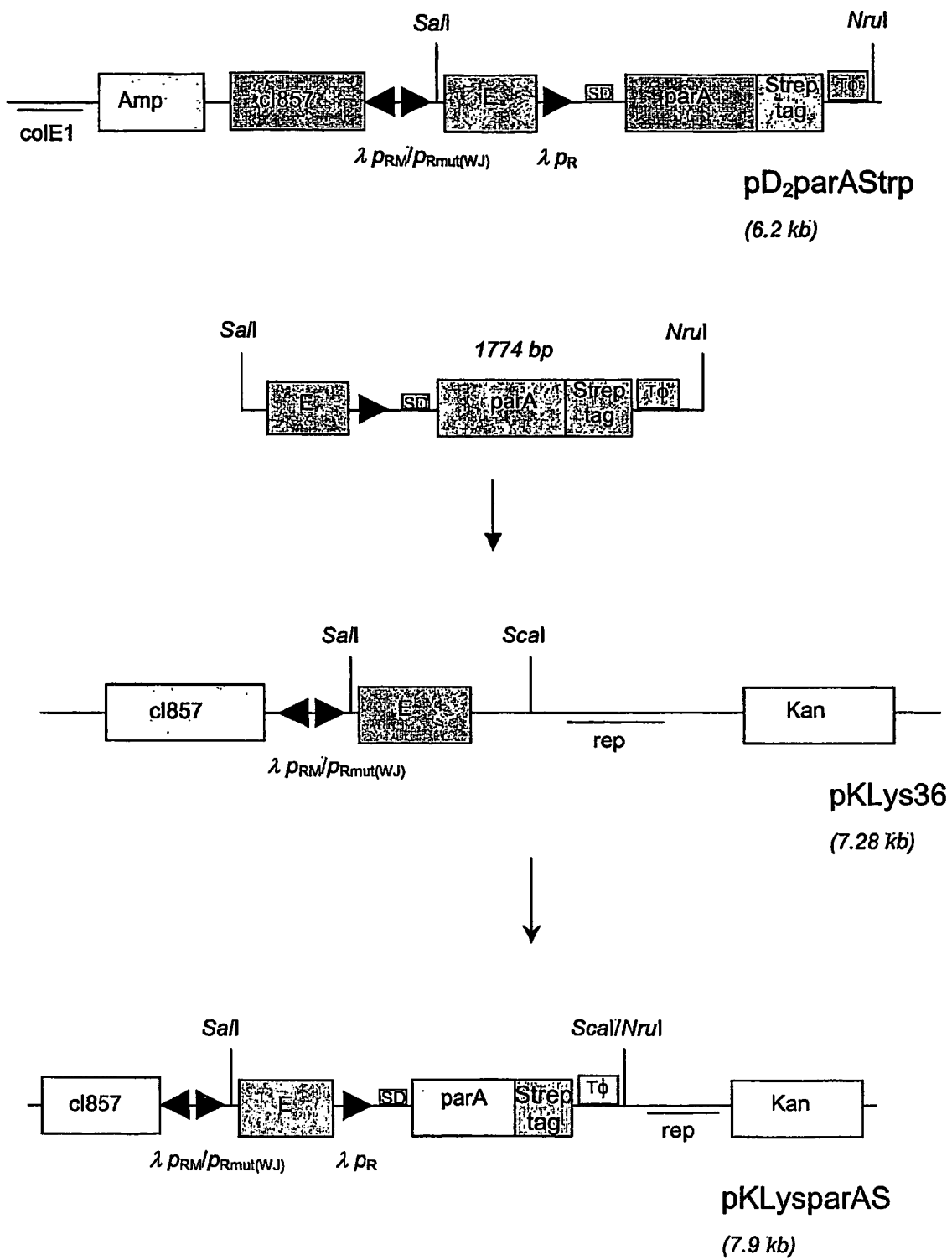

Plasmids pBADparA (Jechlinger, W. Ph.D. Thesis, University of Vienna (2002), pKLys36.1 (Haidinger, W. 2001. PhD. University of Vienna), pKLysparAS (see FIG. 1), pSIPIres (Jechlinger, W., Ph.D. Thesis University of Vienna (2002)), pUC19 (Yanisch-Perron, C. et al. 1985. Improved M13 phage cloning vectors and host strains: nucleotide sequences of the M13mp18 and pUC19 vectors. Gene. 33:103-19), pJMS11 (Panke, S. et al., Engineering of quasi-natural *Pseudomonas putida* strains for toluene metabolism through an ortho-cleavage degradation pathway. Appl Environ Microbiol, 1998. 64(2):748-51), pBAD24 (Guzman, L. M. et al., Tight regulation, modulation, and high-level expression by vectors containing the arabinose PBAD promoter. J Bacteriol, 1995. 177 (14): 4121-30), pSIP (Mayrhofer, P. Ph.D. Thesis University of Vienna (2002)) and *E. coli* strain MC4100 (Silhavy, T. J., Berman et al. 1984. Experiments with Gene Fusions. Cold Spring Harbor Laboratory Press, New York) were used.

Bacteria were grown in Luria broth (LB) and supplemented with ampicillin (200 μg/ml), and kanamycin (50 μg/ml) if appropriate. For gene expression driven by the PBAD promoter the medium was supplemented with 0.5% L-arabinose. Expression of the lysis gene E from vector pKLys36.1 was induced by a temperature shift from 36° to 42° C. Growth and lysis of bacteria was monitored by measurement of the optical density at 600 nm (OD600 nm).

The PCR conditions for generating PCR fragments were as follows: Thirty-five cycles of amplification (45 s at 94° C., 60 s at 60° C. and 1 min-7 min at 72° C.) were performed after 3 min of a predenaturation step at 94° C. in a 100 μl reaction mixture (1×Pfu polymerase buffer containing 2 mM Mg 2+, 2 U of Pfu polymerase, 200 μM dNTP each, 25 pM of each primer and 0.2 μg of plasmid DNA as template). The extension time (72° C.) differed for each construct and is described separately in the following:

Construction of Plasmid pSIPI

To place the resolution sites at the desired positions in the SIP vector it was necessary to introduce suitable restriction sites in plasmid pSIP to enable directional cloning of the resolution sites. Plasmid pSIP was linearised with HindIII and subsequently digested with NaeI. The resulting 2995 bp HindIII/NaeI fragment was eluted from an agarose gel. This fragment contains the regulatory elements of the araBAD operon and the essential elements for self immobilisation. A 3131 bp-DNA fragment containing the β-lactamase gene and origins of replication of M13 and of pBR322 was generated by PCR-amplification (extension time: 7 min) using the primers pSIPI5 (5'-CAGCAGAAGCTTGTTTTGGCGG-ATGAGAGAAG-3') (SEQ ID NO: 1) and pSIPI3 (5'-AGATCTCTGCTGGCGGCCGCGGTTGCTGGC-GCCTATATC-3') (SEQ ID NO: 2) and the vector pSIP as template. Primer pSIPI5 contains a single HindIII site, pSIPI3 contains a BglII and a NotI restriction site. After digestion of the PCR-fragment with HindIII it was ligated with the 2995 bp fragment described above via their blunt site obtained by the Pfu polymerase and the corresponding HindIII site, respectively, resulting in the vector pSIPI. Due to the cloning strategy following restriction sites were introduced: SacII, NotI, BglII, BalI.

Construction of Plasmid pSIPIres

The resolution sites were generated by PCR amplification (extension time: 1 min) using the vector pJMS11 as template and the following primer sets: resolution site 1: 5res1: 5'-CAGCAGCTGCAGCCTTGGTCAAA-TTGGG-TATACC-3' (SEQ ID NO: 3); 3res1: 5'-CTGCTGAAGCT-TGCACATATGTGGGCGTGAG-3' (SEQ ID NO: 4); resolution site 2: 5res2: 5'-CAGCAGGCGGCCGCCCTTGGTCAAAT-TGGGTATACC-3' (SEQ ID NO: 5) 3res2: 5'-CTGCT-GAGATCTGCACATATGTGG GCGTGAG-3' (SEQ ID NO: 6). The PCR-fragment encoding the resolution site 2 contained a unique NotI site at the 5' end and a BglII site at the 3' end and was cloned into the corresponding single sites of pSIPI resulting in the vector pSIPIres2. The resolution site 1 fragment containing a single PstI site at the 5' end and HindIII site at the 3' end, respectively, was then cloned into the corresponding single sites of pSIPIres2 resulting in the vector pSIPIres.

Construction of plasmid pSIPIresHCN

The pBR322 origin of replication in the vector pSIPIres was replaced by the high copy number origin of replication from plasmid pUC19. Therefore the pUC19 origin sequence was amplified by PCR (extension time: 2 min) from pUC19 using primers 5ori (5'-CAGCAGGCCGGCTGAG-CAAAAGGCCAGCA-3') (SEQ ID NO: 7) and 3ori (5'-TGCTGCGCGGCCGCTAGAAAAGATCAAAGGATCT TCTTGAG-3') (SEQ ID NO: 8). The 5ori primer contains a single NaeI site and the 3ori primer a single NotI site. After digestion of the PCR-fragment with NaeI and EagI it was cloned into the corresponding sites of a 4828 bp NaeI/EagI-fragment derived from vector pSIPIres via partial digestion with NaeI and EagI, resulting in the vector pSIPIresHCN (HCN: HighCopyNumber).

Construction of Plasmid pKLysBADparA

A 1920 bp DNA fragment encoding the parA gene under expression control of the arabinose operon was amplified using plasmid pBADparA as template and the primers BAD-KLysfw (5'-ATTCCGACTAGTCAAGCCGTCAAT-TGTCTG 3') (SEQ ID NO: 9) and BADKlysrev (5'-AGC-CCTAGATCTTTATTTTTGCTGCTGCGC 3') (SEQ ID NO: 10) containing terminal SpeI and BglII sites, respectively (extension time: 4 min). The DNA fragment was cloned into the two corresponding sites of the broad host range and low copy plasmid pKLysparAS derived from pKLys36. In this construct (pKLysBADparA) the E-specific lysis cassette of plasmid pKLys36 is flanked by the parA resolvase gene, which is under transcriptional control of the arabinose inducible PBAD promoter (FIG. 2).

EXAMPLE 2

Comparative Example

Figure 2:
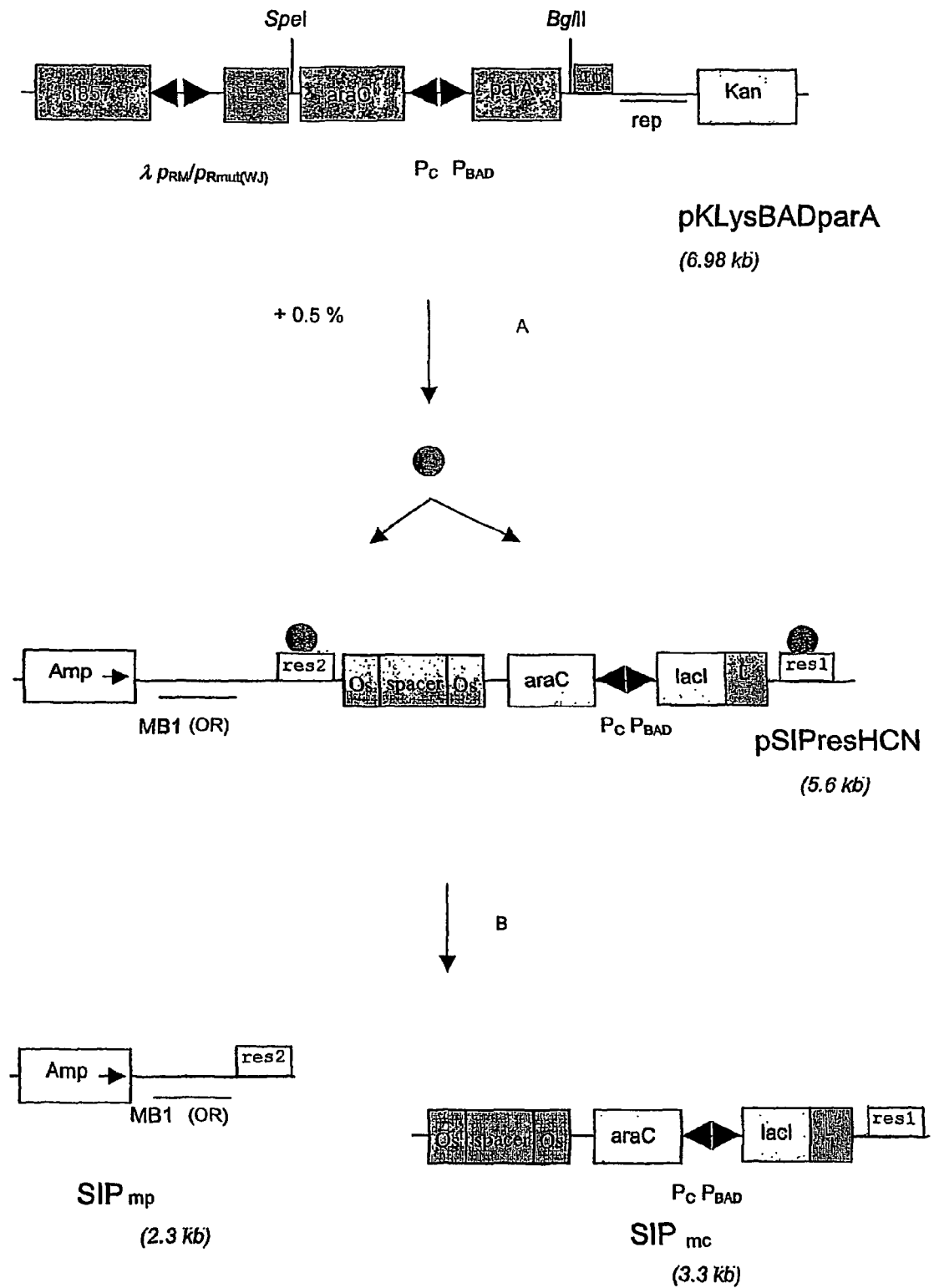
FIG. 2 shows a schematic representation of a designed plasmid.

Production of Minicircles and Miniplasmids with a Resolvase on a Separate Plasmid Plasmids pSIPresHCN and pKLysBADparA were cotransformed in *E. coli* MC4100 (see FIG. 2). The low copy number plasmid pKLysBADparA carries a temperature inducible gene E-specific lysis cassette and the parA resolvase gene under expression control of the arabinose operon. After induction of the resolvase (step "A") it binds to the corresponding resolution sites of plasmid pSIPresHCN, a high copy number plasmid where the resolution sites are flanking the antibiotic resistance gene and the origin of replication (OR). The recombination event (step "B") leads to a partitioning of the original plasmid into a small replicative miniplasmid (mp) and the minicircle (mc) molecule.

Figure 3:
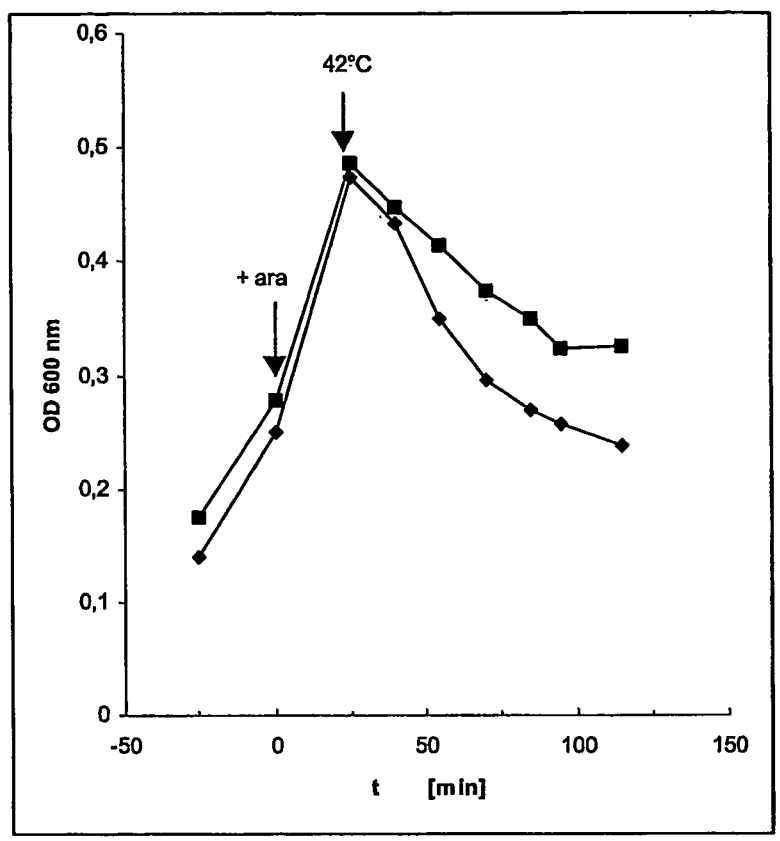
FIG. 3 shows the growth curve of two clones of E. coli.

The high copy number plasmid pSIPresHCN carries the lacIL fusion gene under the transcriptional control of the arabinose operon and the resolution sites flanking the antibiotic resistance gene and the origin of replication. Bacteria were grown at 36° C. and parA expression driven from plasmid pKLysBADparA and the expression of the lacIL' fusion protein driven from plasmid pSIPresHCN, respectively, was induced by addition of 0.5% L-arabinose (FIG. 3). 25 min after addition of expression of the parA resolvase gene bacterial cultures were shifted from 36° C. to 42° C. to induce gene E expression and thus lysis of the cells (FIG. 3). One and two hours after resolvase induction (35 and 95 minutes after lysis induction, respectively) samples were taken from the lysed cultures and plasmids were isolated.

Figure 4:
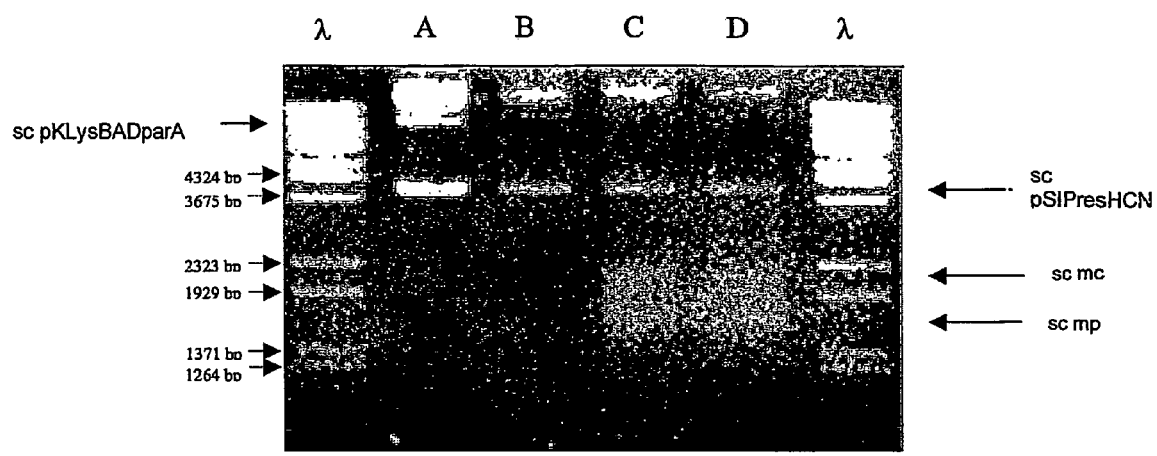
FIG. 4 shows a gel with the bands of supercoiled forms of minicircle and miniplasmid.

To analyse the recombination efficiency aliquots of the DNA precipitations were separated on a 1% agarose gel (FIG. 4): λ, λ BstEII marker; lane A, overnight culture without arabinose. As the plasmid pKLysBADparA is a low copy number plasmid the supercoiled form is hardly visible compared to pSIPresHCN; lane B, before addition of arabinose; lane C and D, 60 and 120 minutes, respectively, after expression of the ParA resolvase. The bands of the supercoiled forms of minicircle and miniplasmid as well as the original pSIPresHCN plasmid are indicated with arrows. It can be seen from FIG. 4 that the supercoiled ("sc") recombined miniplasmid ("mp") and minicircle ("mc") as well as the unrecombined forms of the original plasmid pSIPresHCN can be detected one and two hours after resolvase induction. It was estimated that about 50% of the original high copy number self-immobilised pSIPresHCN plasmids were subjected to recombination with the parA resolvase gene expressed from the low copy plasmid pKLysBADparA.

As the recombinase was produced from a low copy number plasmid with about 10 copies per cell, the amount of resolvase seemed to be not sufficient to achieve an efficient recombination of the high copy number plasmid pSIPresHCN (about 500 copies per cell) containing the corresponding resolution sites. The results were similar to those of Darquet et al. 1997 and Darquet et al. 1999 where a recombinase (the phage lambda integrase) was integrated into the chromosome of *E. coli* as single copy gene. Darquet and his coworkers could recombine about 60% of original plasmids carrying the corresponding lambda attachment sites flanking a therapeutic gene after induction of the single copy integrase gene from the chromosome. Thus the further aim was to place the parA resolvase gene onto the same high copy number plasmid, which also encodes the resolution sites (pSIPresHCN) to overexpress the resolvase and to achieve recombination efficiency close to 100%.

EXAMPLE 3

Minicircle DNA Immobilised in *Escherichia coli* Ghosts

Construction of Plasmid pHCNparA and pBADparA

A 672-bp PCR fragment containing the parA resolvase gene was generated by PCR-amplification (extension time: 2 min). Plasmid pJMSB8 was used as template and primers BADparAfw (5'-ATAGAACCATGGCGACGCGAGAG-CAACAAC 3') (SEQ ID NO: 11) and BADparArev (5'-AGC-CCTCTGCAGTTATTTTTGCTGCTGCGC 3') (SEQ ID NO: 12) to introduce NcoI and PstI restriction sites, respectively. The PCR fragment was cloned into the corresponding sites of plasmid pSIPresHCN, resulting in plasmid pHCN-parA (FIG. 5) and into pBAD24 resulting in pBADparA.

Construction of Plasmid pSIPHCNparA

Using plasmid pBAD24parA as template a 672-bp PCR fragment, which codes for the parA resolvase and the ribosomal binding site derived from pBAD24, was obtained by PCR-amplification (extension time: 2 min). Oligonucleotides HCNparAfw (5'-ACCGAACTGCAGCTACACCATAC-CCGTTTTTTT-GGGC 3') (SEQ ID NO: 13) and HCN-parArev (5'-AGCCCTCTGCAGAAGCTTT-TATTTTTGCTGCTG-CGC 3') (SEQ ID NO: 14) containing PstI and PstI/HindIII as terminal restriction site were used as primers. The fragment was digested with PstI and cloned into the corresponding sites of plasmid pSIPresHCN, resulting in plasmid pSIPHCNparA (FIG. 6).

DNA Precipitation From Culture Supernatant

DNA from the culture supernatant was precipitated with CTAB (cetyltrimethyl-ammonium bromide), modified after Del Sal. 30 ml supernatant of a lysed culture were collected and centrifuged 15 min (15000 rpm, 4° C.). After centrifugation the supernatant was passed through a 0.2 μm sterile filter and precipitated with 2.5 ml 5% CTAB solution in water. After addition of CTAB the DNA was precipitated by centrifugation for 15 min (10000 rpm, 4° C.). The supernatant was discarded and the pellet was resolved in 400 μl 1.2 M NaCl solution. The DNA was precipitated again with 2.5 volumes of 96% EtOH (10 min, 13000 rpm, room temperature, minicentrifuge) and the pellet was washed with 1 ml 70% EtOH. After air-drying, the DNA-pellet was subjected to further purification with the Gel Extraction kit from QIAGEN (according to the instructions of the manufacturer) to remove the bulk of chromosomal DNA.

SDS-PAGE and Western Blotting

Samples (pellets of 1 ml of cultures, resuspended in sample buffer [100×OD600 nm in μl]) were heated to 95° C. for 5 min. in sample buffer and separated on a 12% SDS-polyacrylamid (PAA) gel (10 μl of each sample). Proteins were transferred to nitro-cellulose membranes by semidry-electro-blotting. Proteins were detected with a rabbit polyclonal antiserum to the ParA resolvase protein. Membranes were incubated with primery antibodies (Anti-ParA serum, diluted 1:100 in TBS containing 0.5% BSA [bovine serum albumen], 0.05% NaN3) and secondary antibodies (goat anti-rabbit Alkaline-Phosphatase conjugated antibodies from Sigma diluted 1:5000) for 1 h at room temperature. To stain the antigen-antibody complex, BCIP (5-bromo-4-chloro-3-inod-olyl phosphate) and NTB (nitroblue tetrazolium) from Roche (Roche Diagnostics GmbH, Vienna, Austria) in alkaline phosphatase buffer were used as recommended by the manufacturer. To minimise unspecific binding of the antibodies polyclonal antiserum to the ParA resolvase was incubated with acetone powder derived from the *E. coli* strain MC4100.

Expression of the ParA Resolvase

Figure 7:
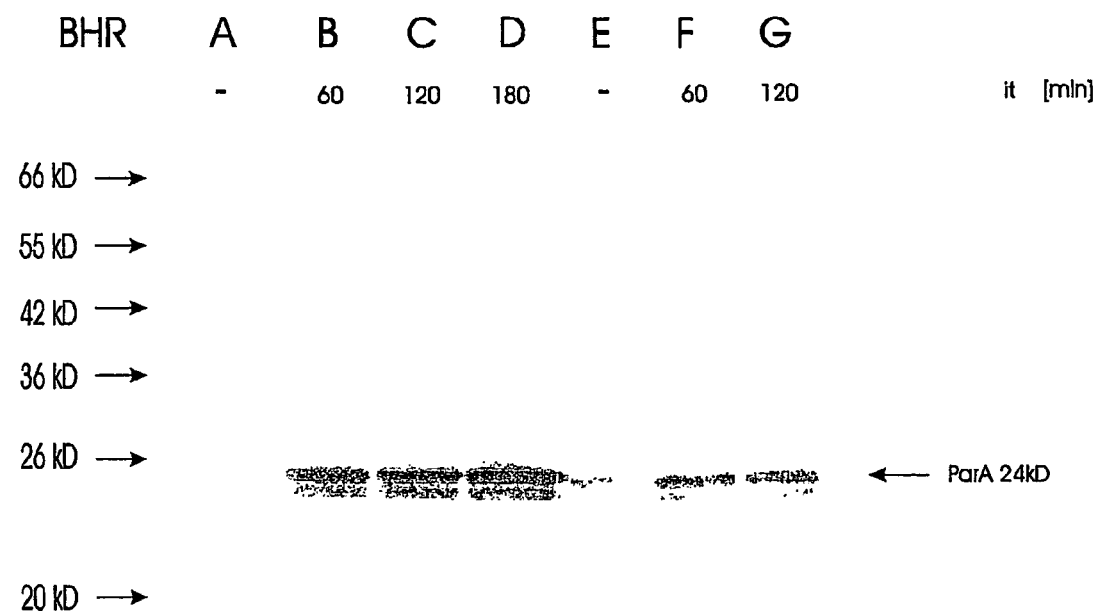
FIG. 7 shows a gel electrophoresis of ParA resolvase.

To determine if the arabinose operon of plasmid pBAD24 may be used for the expression of high levels of resolvase and vice versa for tight repression before induction, the parA resolvase gene was placed under transcriptional control of the araB promoter of the araBAD operon in plasmid pBADparA. Expression of the parA resolvase gene was induced during logarithmical growth of *E. coli* MC4100 (pBADparA) with L-arabinose. Western Blot analysis using ParA specific polyclonal antibodies revealed strong immunoreactive bands at the expected size of 24 kD after 60, 120 and 180 min of induction of parA gene expression (FIG. 7). For this, samples were analyzed using a 12% SDS polyacrylamid gel and immunoblotting with a ParA-specific antiserum. lane BHR, broad host range proteinmarker; lanes A-D, *E. coli* NM522 (pBADparA) grown with and without arabinose, respectively; lanes E-G, *E. coli* NM522 (pJMSB8) grown with and without IPTG, respectively. Before induction no specific immunoreactive protein band could be detected. For a positive control *E. coli* MC4100 (pJMSB8) were grown logarithmically and by addition of IPTG expression of the parA resolvase expression was induced. Protein bands specific for the ParA resolvase could be determined 60 and 120 min after induction ("it"=induction time) but also prior to the induction a background expression of the recombinase could be observed.

Figure 5:
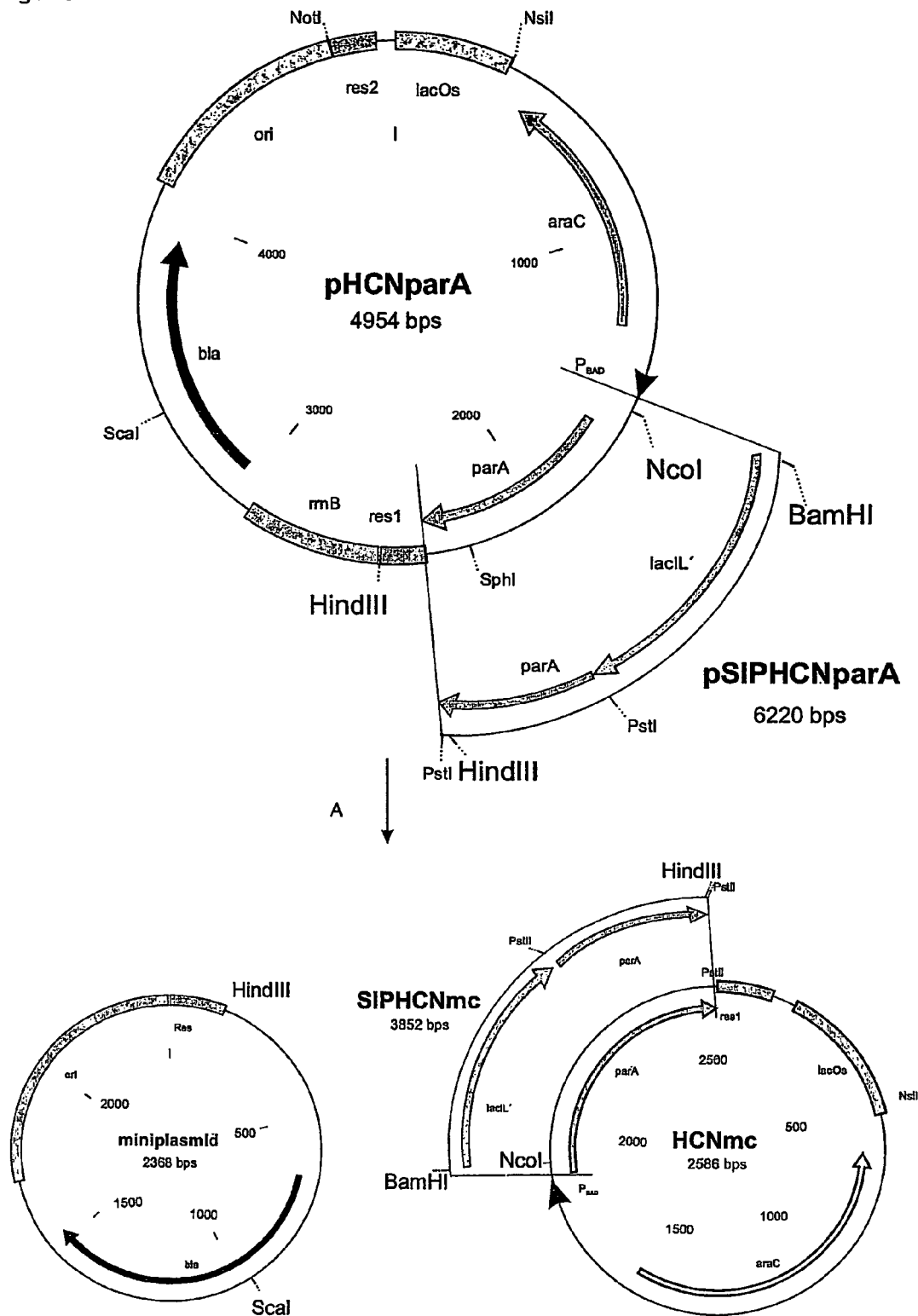
FIGS. 5 and 6 show schematic representations of plasmid constructions.
Figure 8:
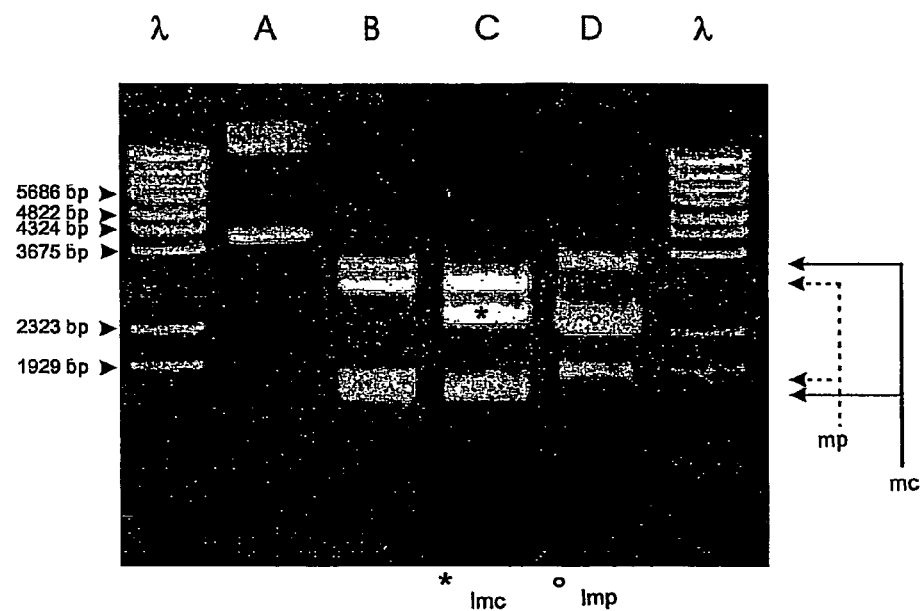
FIGS. 8 and 9 show gel electrophoresis of minicircles and miniplasmids.
Figure 8:
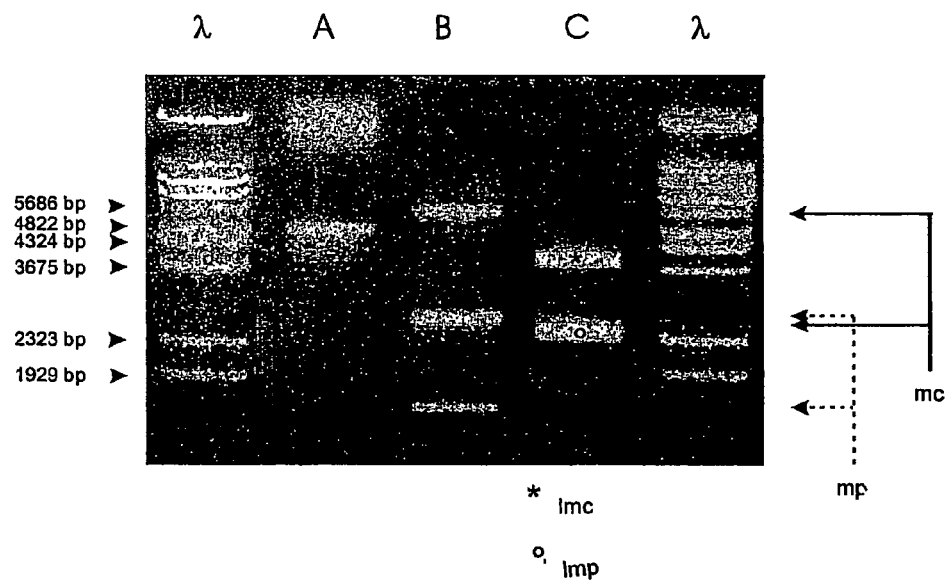

In Vivo Minicircle Production in *E. coli* MC4100 (pHCN-parA) As the arabinose expression system seemed to be suitable for high level expression and tight repression of the parA resolvase gene in plasmid pBADparA, the recombination efficiency was evaluated with plasmid pHCNparA. In plasmid pHCNparA the resolvase was placed under the expression control of the araB promoter. Furthermore, the origin of replication and the ampicillin resistance gene are flanked by the resolution sites on the same plasmid (FIG. 5). Plasmids pHC-NparA, pSIPHCNparA and the products of the recombination driven by the parA resolvase (step "A"). HCNmc, minicircle derived from origin plasmid pHCNparA; SIPHC-Nmc, minicircle derived from origin plasmid pSIPHCNparA; bla, ampicillin resistance gene; ori, origin of replication derived from pUC19; parA, parA resolvase gene; lacI-L', fusion gene of lacI repressor gene with bacteriophage MS2 L' anchor sequence; PBAD, arabinose-inducible promoter; araC, repressor/inducer of the PBAD promoter; lacOs, altered lac operator sequences with high affinity to the LacI repressor protein; res1, res2, resolution sites, sequences recognised by the ParA resolvase; rrnB, transcriptional terminators of the 5S ribosomal gene. After induction of the parA resolvase gene a complete separation based on recombination of the original plasmid into a minicircle ("mc") and a miniplasmid ("mp") could be observed by plasmid analysis 30 minutes after induction of the resolvase (FIG. 8A): λ, λ BstEII marker; lane A, before addition of arabinose; lane B, 30 min after induction of the parA resolvase. The double bands of the relaxed and supercoiled forms of minicircle and miniplasmid are indicated with arrows; lane C, 30 minutes after expression of the ParA resolvase digested with NcoI. The minicircle was linearised ("L") and the miniplasmid remained undigested. lane D, 30 minutes after expression of the ParA resolvase digested with HindIII. The miniplasmid was linearised and the minicircle remained undigested. FIG. 8B: DNA preparations of E. coli MC4100 (pSIPHCNparA), whereby λ, λ BstEII marker; lane A, before addition of arabinose; lane B, 30 minutes after expression of the ParA resolvase. The double bands of the relaxed and supercoiled forms of minicircle and miniplasmid are indicated with arrows; lane C, 30 minutes after expression of the ParA resolvase digested with HindIII. The minicircle and the miniplasmid were linearised.

Before induction no recombination events could be detected (FIG. 8A). In FIG. 8A the relaxed and supercoiled forms of the circular miniplasmid and minicircle are shown 30 minutes after induction of the parA resolvase gene, whereas no original plasmid was detected. Restriction analysis of the miniplasmid and minicircle revealed the expected sizes of the linearised forms (FIG. 8A).

In Vivo SIP-Minicircle Production in E. coli MC4100 (pSIPHCNparA)

After evaluating the recombination efficiency with plasmid pHCNparA the parA resolvase together with the lacI-L' hybrid gene was brought under expression control of the araB promoter as polycistron in plasmid pSIPHCNparA, which also contains the origin of replication and the ampicillin resistance gene flanked by the resolution sites (FIG. 5). By inducing the gene expression, the lacI-L' hybrid gene as well as the recombinase gene should be expressed simultaneously. After induction of the production of membrane-anchored LacI and the resolvase with L-arabinose in growing cultures of E. coli NM522 (pSIPHCNparA) a complete recombination of the original plasmid into a miniplasmid and minicircle could be detected 30 minutes after induction of the resolvase (FIG. 8B). The double bands of the relaxed and supercoiled forms of minicircle and miniplasmid are indicated with arrows in FIG. 8B. As in pSIPHCNparA the res1 sequence is flanked by HindIII sites (FIG. 5), the minicircle as well as the miniplasmid were linearised when digested with HindIII. The linearised miniplasmid and minicircle showed the expected sizes (FIG. 8B).

Self Immobilisation of Minicircle DNA in Bacterial Ghosts

A system with two compatible vectors is used for the in vivo immobilisation of the minicircle DNA. One vector, the starting plasmid, codes for elements for the production of the minicircle DNA as well as for the necessary components for the anchorage of the elements in the bacterial cytoplasmatic membrane. The desired sequences for the gene therapy or for vaccination may be cloned into this vector. The second vector codes for the sequence necessary for bacterial lysis (protein E as well as corresponding regulatory components). To separate the process of plasmid immobilisation and the protein E mediating lysis, both vectors must be inducible independently.

Figure 6A:
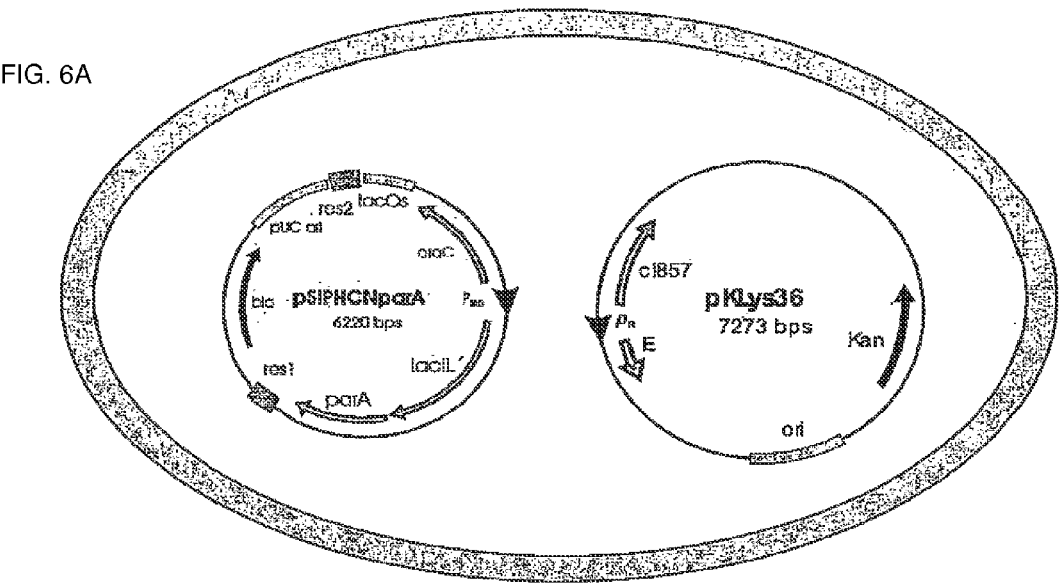

The starting plasmid for this process (pSIPHCNparA) illustrated in FIG. 5 comprises an additional component (LacI-L') for the immobilisation of the minicircle DNA (compare FIG. 6A). Additionally, the plasmid codes for the repressor of the Lactose Operon (LacI), to which on the 3' site the the last 56 C-terminal amino acids of the lysis protein L (L') of the bacteriophage MS2 was cloned. This fusion protein (LacI-L') is also kept under control of of the promoter of the Arabinose Operon (P$_{BAD}$). By induction of the P$_{BAD}$ promoter with L-Arabinose a bicistrionic mRNA is produced, coding for ParA resolvase as well as for LacI-L' fusion protein. As described above, the expressed ParA resolvase splits the starting plasmid into miniplasmid and minicircle. The LacI-L' fusion protein binds to the minicircle DNA. The tandem repeat of the lacOs sequence serves as binding site for LacI-L'. Due to the fusion with the hydrophobic peptide L' the repressor and therefore the bound plasmid is directly anchored in the bacterial membrane (compare FIG. 6A).

The lysis plasmid codes for gene E of the bacteriophage φX174 (compare FIG. 6A—pKLys36). The gene product, protein E, is a hydrophobic polypeptide with 91 amino acids and a molecular weight of about 10 kD (Barrell et al.; Nature 264 (1976), 34-41). By expression of a plasmid coded protein E a channel structure with 40 to 200 nm diameter ist formed in the membrane of the plasmid producing bacteria (E. coli). The E-lysis channel is characterised by a narrow opening in the membrane complex of E. coli. The formation of the channel is associated with a fusion of the inner and outer membrane (Witte et al., J. Bacteriol. 172 (1990), 4109-4117). Impelled by the osmotic pressure in the cell inside cytoplasmatic components are expelled into the culturing medium with the protein E mediating lysis. Witte und Lubitz (Eur. J. Biochem. 180 (1989), 383-398) were able to show that 20 minutes after induction of the protein E expression about 90% of the cytoplasmatic protein β-galactosidase in the culturing supernatant were present. Additionally, chromosomal DNA, fractionised due to the shear stress acting during lysis into fragments of 30 to 40 kbp, supercoiled plasmid DNA as well as tRNA and rRNA could also be proven in the culturing supernatant. Empty bacterium envelopes produced by protein E mediating lysis are called ghosts. Plasmids having been immobilised before the induction of the lysis in the cytoplasmatic membrane of the host bacterium are not expelled into the culturing medium during the lysis process, because they are anchored to the cytoplasmatic membrane of the bacterium ghosts (compare FIG. 5 (Mayrhofer (2002) and Jechlinger (2002) Ph.D. Theses, see above). The described principle of separation into a miniplasmid and a minicircle also persists in this process. The basic difference lies in that the minicircle with this further development of the process is in vivo immobilised in the bacterial cytoplasmatic membrane. The benefit of immobilisation lies in the fact that the bacteria cells producing plasmid may be lysed by formation of a transmembranal channel structure. During this lysis process the most part of the cytoplasmatic components are expelled into the culturing medium, while the DNA minicircle remains anchored to the host cell. Thereby a preliminary purification, i.e. a separation of the miniplasmid DNA as well as undesirable nucleic acids of the host cell, is achieved. The DNA minicircles anchored to the bacteria ghosts may be dissected by standard processes and be isolated subsequently.

Figure 6B:
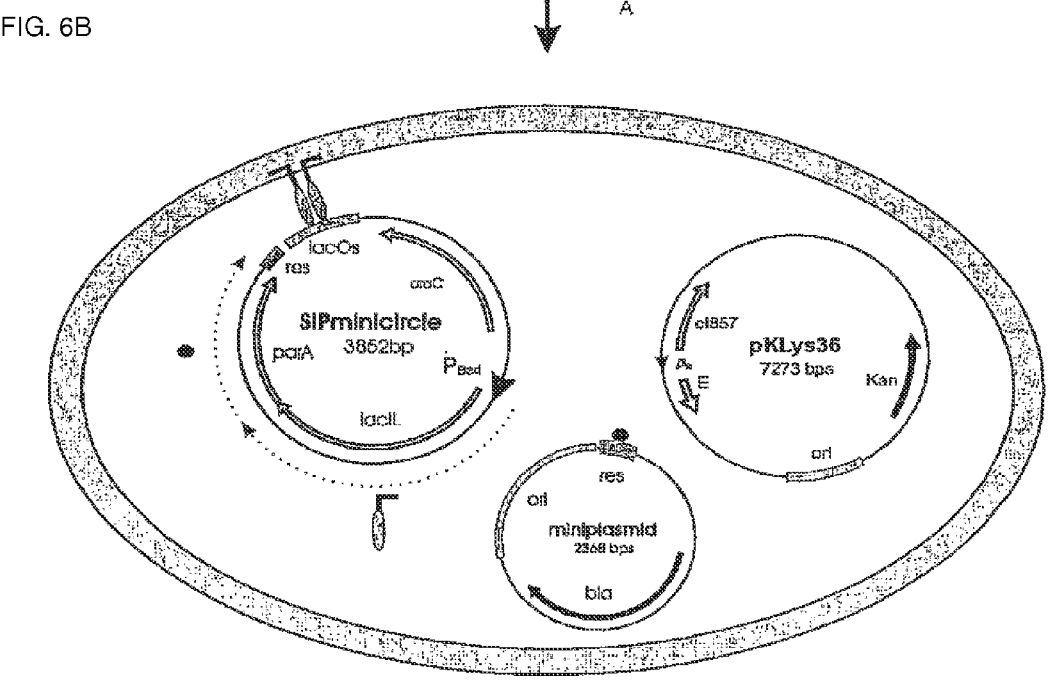
Figure 6C:
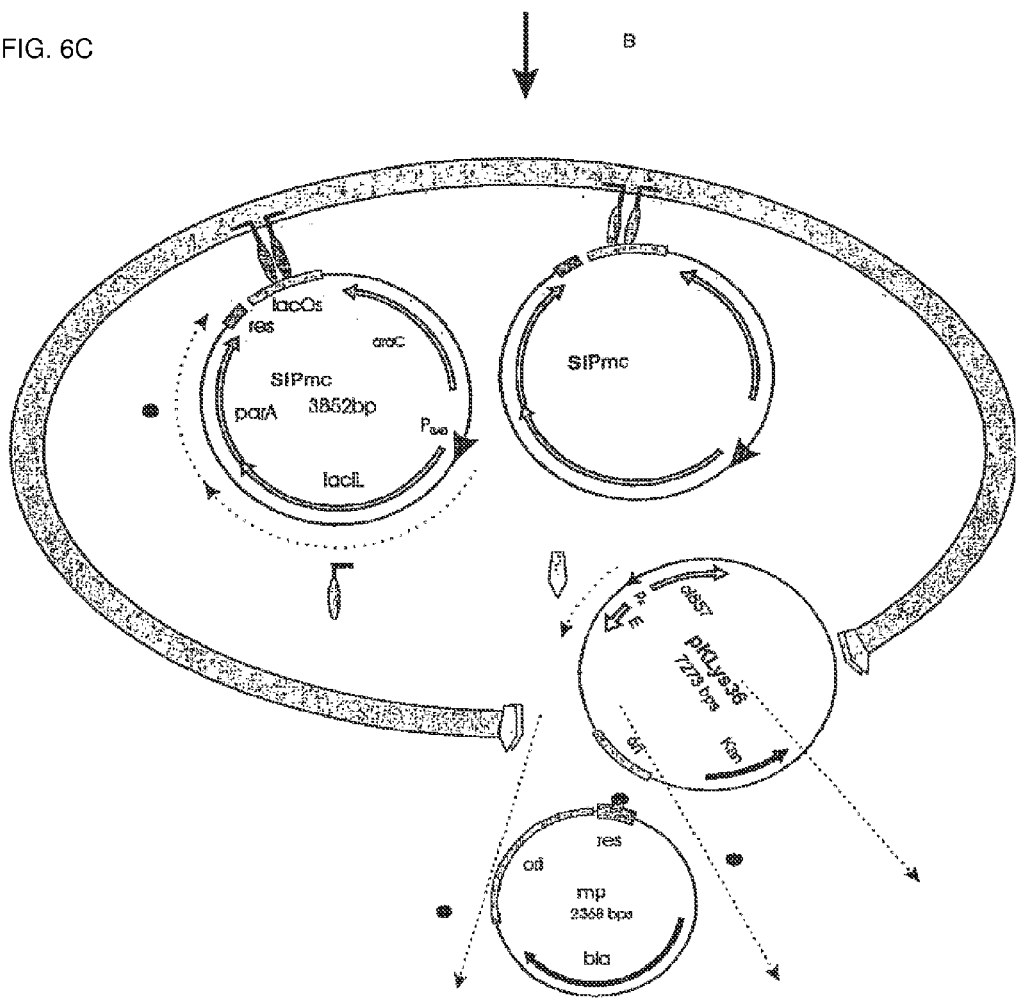

To produce bacterial ghosts in combination with the self immobilisation of the minicircle, according to the present example bacteria were cotransformed with pSIPHCNparA and pKLys36, a lysis plasmid carrying an E-specific lysis cassette where gene E is under expression control of the λ$_{pRmutWJ}$ promoter and the temperature-sensitive cI857 repressor (FIG. 6A): The E. coli NM522 cells are cotransformed with the self immobilisation plasmid (pSIPHCN-parA) and a compatible lysis plasmid (pKLys36.1). FIG. 6B: The ParA resolvase and the LacI-L' membrane anchor are expressed and the resolvase excises the origin of replication and the antibiotic resistance gene of the origin plasmid resulting in a replicative miniplasmid and the minicircle. The LacI-L' fusion protein integrates in the inner membrane and the minicircles bind to the LacI protein via the lac operator sites. C: Lysis is induced by gene E expression and the cytoplasmatic material together with non immobilised plasmids is released through the transmembrane tunnel structure resulting in bacterial ghosts carrying DNA minicircles in the inner membrane.

Figure 9:
Figure 9:
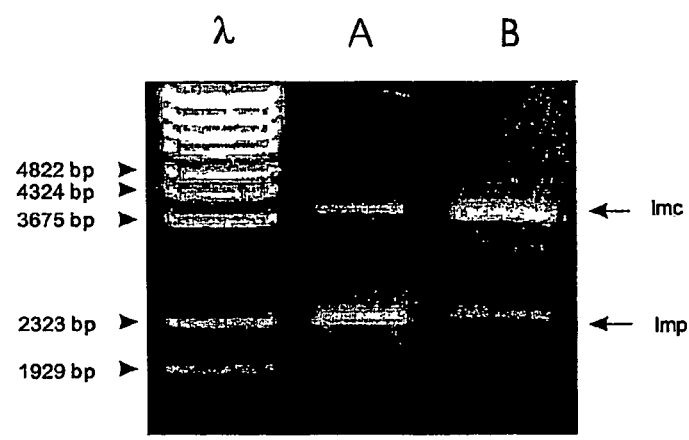

Ten min after the induction of the expression of the lacI-L' hybrid gene and the parA resolvase gene (FIG. 6B) (step "A"), the E-lysis was induced by shifting the temperature from 36° C. to 42° C. (FIG. 6C) (step "B"). A control was grown at 36° C. without inducing lysis by temperature upshift. DNA was precipitated from the supernatants and the pellets to investigate whether the miniplasmid leaves the cell through the lysis hole whereas the minicircle is retained in the bacterial ghosts due to interaction between the lac operator sequences and the LacI protein anchored to the inner membrane. In FIG. 9 it is shown that 10 and 30 min after induction of lysis both DNA molecules, the miniplasmid and the minicircle, could be detected in the supernatant and the pellets in different amounts:

FIG. 9A: Preparation of DNA from pellets and supernatants of E. coli MC4100 (pSIPHCNparA, pKLys36.1): 10 min (lanes A and B) and 30 min (lanes D and E) after induction of E-mediated lysis (20 and 40 min after addition of L-arabinose, respectively). As control E. coli MC4100 (pSIPHCNparA, pKLys36.1) was grown at 36° C. and 20 (lane C) and 40 minutes (lane F) after addition of L-arabinose DNA preparations were analyzed. λ, λ BstEII marker. Mainly the smaller miniplasmid could be detected in the supernatants; mainly the minicircles could be detected in the pellets. Whereas 20 min after induction of the resolvase both DNA molecules could be detected at equal amounts, the amount of the replicative miniplasmid was increasing 40 min after resolvase induction. FIG. 9B: Inversely proportional amount of miniplasmid and minicircle in the supernatant and pellets of lysates of E. coli MC4100 (pSIPHCNparA, pKLys36.1) 30 min after induction of E-mediated lysis digested with ScaI and BamHI. λ, λ BstEII marker; lane A, aliqout of DNA preparation of the supernatant digested with ScaI and BamHI, both DNA molecules are linearised, mainly the smaller miniplasmid could be detected in the supernatant; lane B, aliqout of DNA minipreparation of pellets digested with ScaI and BamHI, mainly the minicircle could be detected in the pellets.

In the preparation of the supernatant the replicative miniplasmid was found in large amounts, whereas in the pellets, the bacterial ghosts, mostly the immobilised minicircle was detected. The at each case other DNA molecule could only be detected as a faint band. These results indicated that most of the minicircle was retained in the bacterial ghosts during the lysis procedure and could be found in the pellets of the lysate, whereas the majority of the miniplasmids was expelled through the lysis pores and could be detected in the supernatant. This inversely proportional amount of miniplasmid and minicircle in the supernatant and pellets was confirmed when both preparations were cut with restriction enzymes ScaI and BamHI to linearise the DNA molecules (FIG. 9B). As expected the pellet DNA preparations of the control which was further grown at 36° C. revealed that the amount of miniplasmid in the cells was increasing compared to the minicircles as the miniplasmid was able to replicate in contrast to the minicircle (FIG. 9A). As the control culture was not shifted to 42° C. and therefore no E-specific pores were produced in the bacteria the miniplasmids could not leave the growing cells.

The invention claimed is:

1. A plasmid comprising the following functional units:
a prokaryotic origin of replication,
a marker sequence,
two specific recombinase recognition sequences and
a multiple cloning site,
a regulatory element for the expression of a recombinase characterised in that it comprises a gene coding for a sequence specific recombinase, a minicircle identification sequence for the identification and isolation of a minicircle and/or a miniplasmid identification sequence for the identification, isolation and removal of a miniplasmid and wherein a gene coding for a specific protein is inserted into the multiple cloning site,
whereby the units are arranged on the plasmid in such a way that the plasmid is divided into a miniplasmid and a minicircle upon induction of the expression of the sequence specific recombinase via the regulatory element, said miniplasmid comprising the prokaryotic origin of replication, the marker sequence and the gene for the sequence specific recombinase and said minicircle comprising the multiple cloning site,
wherein the sequence specific recombinase is ParA resolvase.

2. The plasmid according to claim 1, characterised in that a gene coding for a therapeutically useful protein, is inserted into the multiple cloning site.

3. The plasmid according to claim 1, characterised in that the minicircle identification sequence and the miniplasmid identification sequence are sequences which are able to specifically bind to a protein in order to form a stable DNA-protein complex.

4. The plasmid according to claim 3, characterised in that the minicircle identification sequence or the miniplasmid identification sequence is a lac operator site which specifically binds to a LacI repressor protein.

5. The plasmid according to claim 3 or 4, characterised in that it further comprises a gene coding for the protein which forms the DNA-protein complex, preferably a gene coding for the LacI repressor protein.

6. The plasmid according to claim 1, characterised in that the regulatory element is a transcriptional control system of an araB promoter of an araBAD operon.

7. The plasmid according to claim 1, characterised in that the marker gene is an antibiotic resistance gene.

8. The plasmid according to claim 1, characterised in that the prokaryotic origin of replication is a high copy number origin of replication, preferably from plasmid pUC19.

9. The plasmid according to claim 1, wherein the minicircle comprises an origin of replication.

10. A kit for the production of a therapeutically useful DNA molecule, comprising
the plasmid according to claim 3 and
a protein which is able to bind to the identification sequence of the plasmid in order to form a stable DNA-protein complex, whereby the protein is optionally immobilised to a solid support.

11. The kit according to claim 10, characterised in that the protein is a LacI repressor protein, preferably a mutant LacI repressor protein.

12. The kit according to claim 10, characterised in that the protein is fused to a tag for the immobilisation to a solid support.

13. The kit according to claim 10, characterized in that it comprises a separate plasmid carrying an inducible lysis gene or wherein the plasmid comprises an inducible lysis gene and further comprises a culture of recombinant bacteria transfected with said plasmid.

14. The kit according to claim 13, characterised in that the lysis gene is the lysis gene E of bacteriophage PhiX174.

15. The kit according to claim 10, further comprising a culture of bacteria specific for the expression and function of the recombinase.

16. The kit according to claim 10, further comprising arabinose.

17. A method for the production of a therapeutically useful DNA molecule, comprising
transfecting the plasmid according to claim 2 into bacteria to replicate the plasmid,
culturing the bacteria during which the recombinase is expressed upon induction of the regulatory element so that miniplasmids and minicircles are produced and
isolating the minicircles.

18. The method according to claim 17, wherein the minicircles are isolated by using a minicircle identification sequence.

19. The method according to claim 17, wherein the minicircles are isolated by immobilisation to a solid support.

20. The method according to claim 17, characterised in that the recombinase is expressed upon induction of the regulatory element by adding arabinose to the culture medium.

21. The method according to claim 17, wherein a protein recognising the minicircle identification sequence is further expressed in the bacteria and anchored in the bacterial membrane so as to bind to the minicircles.

22. The method according to claim 19, wherein the minicircles are isolated by a chromatography column.

\* \* \* \* \*